United States Patent
Alvarez

(10) Patent No.: US 7,820,183 B2
(45) Date of Patent: *Oct. 26, 2010

(54) BOTULINUM TOXIN IN TREATMENT OF CLUBFOOT RELAPSE

(75) Inventor: Christine M. Alvarez, Vancouver (CA)

(73) Assignee: Allergan, Inc., Irvine, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/504,198

(22) Filed: Aug. 15, 2006

(65) Prior Publication Data

US 2007/0088320 A1 Apr. 19, 2007

Related U.S. Application Data

(60) Provisional application No. 60/709,451, filed on Aug. 19, 2005.

(51) Int. Cl.
*A61K 39/08* (2006.01)
*C07K 14/00* (2006.01)

(52) U.S. Cl. .................. 424/239.1; 424/236.1; 424/9.1; 514/2; 514/12; 530/350; 435/252.7

(58) Field of Classification Search .............. 424/239.1, 424/236.1, 9.1; 514/2, 12; 530/350; 435/252.7
See application file for complete search history.

(56) References Cited

OTHER PUBLICATIONS

Alkjaer T, Pedersen EN, Simonsen EB. Evaluation of the walking pattern in clubfoot patients who received early intensive treatment. J Pediatr Orthop. 2000;20:642-647.
Applington JP, Riddle CD. Avascular necrosis of the body of the talus after combined medial and lateral release of congenital clubfoot. South Med J. 1976;69:1037-1038.
Asperheim MS, Moore N, Carroll NC, et al. Evaluation of residual clubfoot deformities using gait analysis. J Pediatr Orthop B. 1995;4:49-54.
Atar D, Lehman WB, Grant AD. Complications in clubfoot surgery. Orthop Rev. 1991;20:233-239.
Bakheit AM, Severa S, Cosgrove A, et al. Safety profile and efficacy of Botulinum toxin A (Dysport) in children with muscle spasticity. Dev Med Child Neurol. 2001;43:234-238.
Bang MS, Chung SG, Kim SB, et al. Change of dynamic gastrocnemius and soleus muscle length after block of spastic muscle in cerebral palsy. Am J Phys Med Rehabil. 2002;81:760-764.
Bensahel H, Guillaume A, Desgrippes Y. Results of physical therapy for idiopathic clubfoot: a longterm follow up. Journal of Pediatric Orthopaedics 1990;10:189-192.
Brin MF, ed. Spasticity: etiology, evaluation, management, and the role of botulinum toxin A. Muscle Nerve. 1997;20(Supp 6):61-91.
Carroll NC. Surgical technique for talipes equinovarus. Oper Tech Orthop. 1993;3:115-120.
Chotel F, Parot R, Durand J, et al. Initial management of congenital varus clubfoot by Ponseti's method. Rev Chir Orthop Reparatrice Appar Mot. 2002;88:710-717.
Cooper DM, Dietz FR. Treatment of idiopathic clubfeet: a thirty-year follow-up note. J Bone Joint Surg [Am]. 1995;77:1477-1489.
Crawford AH, Marxen JL, Osterfeld DL. The Cincinnati incision; a comprehensive approach for surgical procedures of the foot and ankle in childhood. J Bone Joint Surg [Am]. 1982;64:1355-1358.
Delgado et al. A preliminary report of the use of botulinum toxin type A in infants with clubfoot: four case studies. Journal of Pediatric Orthopedics. 2000;20(4):533-8.
Delgado, M.R., et al., A preliminary report of the use of botulinum toxin type A in infants with clubfoot: fouir case studies, Journal of Pediatric Orthopedics, Jul.-Aug. 2000, vol. 20, No. 4, pp. 533-538.
Dimeglio A, Bensahel H, Souchet PH, Mazeau P, Bonnet F. Classification of clubfoot. Journal of Pediatric Orthopaedics (Br) 1995;4:129-136.
Eames NW, Baker R, Hill N, et al. The effect of botulinum A toxin on gastrocnemius length: magnitude and duration of effect. Dev Med Child Neurol. 1999;41:226-232.
Edgar TS. Clinical utility of botulinum toxin in the treatment of cerebral palsy: comprehensive review. J Child Neurol. 2001;16:37-46.
Flynn JM et al. An independent assessment of two clubfoot-classification systems. Journal of Pediatric Orthopedics. 18(3):323-7, 1998.
Goksan SB. Treatment of congenital clubfoot with the Ponseti method. Acta Orthop Traumatol Turc. 2002;36:281-287.
Hee HT, Lee EH, Lee GS. Gait and pedographic patterns of surgically treated clubfeet. J Foot Ankle Surg. 2001;40:287-294.
Herzenberg JE, Radler CR, Bor N. Ponseti versus traditional methods of casting for idiopathic clubfeet. J Pediatr Orthop. 2002;22:517-521.
Johnson L, ed. Essential Medical Physiology, 2nd ed. Philadelphia: Lippincott-Raven, 1998.
Juzans P, Comella JX, Molgo J, et al. Nerve terminal sprouting in botulinum A-treated mouse levator auris longus muscle. Neuromuscul Disord. 1996;6:177-185.
Karol LA, Concha MC, Johnston C.E.2nd. Gait analysis and muscle strength in children with surgically treated clubfeet. Journal of Pediatric Orthopaedics 1997;6:790-795.
Klein AW. Complications and adverse reactions with the use of botulinum toxin. Semin Cutan Med Surg. 2001;20:109-120.
Koman LA, Mooney JF, Smith B, et al. Management of cerebral palsy with botulinum A toxin: preliminary investigation. J Pediatr Orthop. 1993;13:489-495.
Laaveg SJ, Ponseti IV. Long-term results of treatment of congenital clubfoot. J Bone Joint Surg [Am]. 1980;62:23-31.
McKay DW. New concept of and approach to clubfoot treatment: section II. Correction of the clubfoot. J Pediatr Orthop. 1983;3:10-21.
McNeer KW, Tucker MG, Spencer RF. Management of essential infantile esotropia with botulinum toxin A: review and recommendations. J Pediatr Ophthalmol Strabismus. 2000;37:63-67.

(Continued)

*Primary Examiner*—Chih-Min Kam
(74) *Attorney, Agent, or Firm*—Claude L. Nassif; Debra Condino; Stephen Donovan

(57) ABSTRACT

Botulinum toxin, or other neuromuscular inhibitors, injected into the lower leg muscle of infants, less than a year old, with idiopathic clubfoot is shown to be an effective therapy in correcting this physical deformity. Following a protocol of manipulations, castings, and injections, clubfoot is effectively treated, and surgical treatment procedures can be avoided.

20 Claims, 4 Drawing Sheets

OTHER PUBLICATIONS

Miller JH, Bernstein SM. The roentgenographic appearance of the corrected clubfoot. Foot Ankle. 1986;6:177-183.

Mooney JF, Koman LA, Smith BP. Pharmacologic management of spasticity in cerebral palsy. J Pediatr Orthop. 2003;23:679-686.

Morrissy RT, Weinstein SL, eds. Lovell and Winter's Pediatric Orthopaedics, 2nd ed. Philadelphia: Lippincott-Raven, 1996.

Otis JC, Bohne WH. Gait analysis in surgically treated clubfoot. J Pediatr Orthop. 1986;6:162-164.

Piers, Mitchell D., et al., Selective botulinum toxin injection in the treatment of recurrent deformity following surgical correction of cloub foot—A preliminary report of 3 children, Acta Orthopaedica Scandinavica, vol. 75, No. 5, Oct. 2004, pp. 630-633.

Ponseti IV. Clubfoot management. J Pediatr Orthop. 2000;20:699-700.

Ponseti IV. Common errors in the treatment of congenital clubfoot. Int Orthop. 1997;21:137-141.

Ponseti IV. Congenital Clubfoot: Fundamentals of Treatment. New York: Oxford University Press, 1996.

Ponseti IV. Treatment of congenital clubfoot. J Bone Joint Surg [Am]. 1992;74:448-454.

Reiter, F, Danni, M., Lagalla, G., Ceravolo, G., Provinciali, L. 1998. Low dose botulinum toxin eith ankle taping for the treatment of spastic equinovarus foot after stroke. Arch Phys Med Rehabil 79:532-535.

Roye DP, Roye BD. Idiopathic congenital talipes equinovarus. J Am Acad Orthop Surg. 2002;10:239-248.

Schlafly B, Butler JE, Siff SJ. The appearance of the tarsal navicular after posteromedial release for clubfoot. Foot Ankle. 1985;5:222-237.

Scott AB. Botulinum A injection of eye muscles to correct strabismus. Trans Am Ophthalmol Soc. 1981;79:734-770.

Seringe R, Atia R. Idiopathic congenital clubfoot. Results of functional treatment. *Revue de Chirurgie Orthopedique et Reparatrice de l'Appareil Moteur* 1990;76:490-501.

Souchet P, Bensahel H, Themar-Noel C, Pennecot G, Csukonyi Z. Functional treatment of clubfoot: A new series of 350 idiopathic clubfeet with long-term follow-up. *Journal of Pediatric Orthopaedics (Br)* 2004;13:189-196.

Turco VJ. Surgical correction of the resistant clubfoot: one-stage posteromedial release with internal fixation. A preliminary report. J Bone Joint Surg [Am]. 1971;53:477-497.

Widhe T, Berggren I. Gait analysis and dynamic foot pressure in the assessment of the treated clubfoot. Foot Ankle Int. 1994;15:186-190.

Alvarez, Christine M., et al., *Treatment of Idiopathic Clubfoot Utilizing Botulinum A Toxin*, J. Pediatr Orthop, vol. 25, No. 2, Mar./Apr. 2005, pp. 229-234.

Bleck, E. Metatarsus adductus: Classification and relationship to outcomes of treatment. Journal of Pediatric Orthopedics 1983;3:2-9.

Carroll NC, McMurtry R, Leete SF. The pathoanatomy of congenital clubfoot. Orthop Clin North Am. 1978;9:225-232.

Dobbs MB. A single surgeon's experience with the Ponseti method for the treatment of idiopathic clubfoot deformity. International Society of Orthopedic Surgery and Traumatology 3rd International Clubfoot Congress, San Diego, California, Aug. 2002.

Garceau, G, Palmer, R. Transfer of the anterior tibial tendon for recurrent clubfoot: A long-term follow-up. Journal of Bone and Joint Surgery 1967;49:207-31.

Garceau, G. Anterior tibial tendon transfer for recurrent clubfoot. *Clinical ,Orthopedics and Related Research* 1 972;84:61 .5.

Karol LA, Concha MC, Johnston CE 2d. Gait analysis and muscle strength in children with surgically treated clubfeet. J Pediatric Orthopetic. 1997;6:790-795.

Lehman WB, Scher DM, Feldman DS, et al. Method of evaluating the effectiveness of the Iowa (Ponseti) clubfoot technique. International Society of Orthopedic Surgery and Traumatology 3rd International Clubfoot Congress, San Diego, California, Aug. 2002.

Morcuende JA, Dolan LA, Ponseti IV. Efficacy of the Ponseti method in the treatment of idiopathic clubfoot. International Society of Orthopedic Surgery and Traumatology 3rd International Clubfoot Congress, San Diego, California, Aug. 2002.

Pirani S, Outerbridge H, Moran M, Sawatsky BJ. A method of evaluating the virgin clubfoot with substantial inter observer reliability. Pediatric Orthopedic Society of North America 1995 Annual Meeting, Miami, Florida, May 1995.

U.S. Appl. No. 11/504,199, filed Aug. 15, 2006, Alvarez, C.

Pirani S. Ponseti treatment of the congenital clubfoot: the New Westminster experience. International Society of Orthopedic Surgery and Traumatology 3rd International Clubfoot Congress, San Diego, California, Aug. 2002.

Richards BS, Wilson H. Non-operative clubfoot treatment using physical therapy. International Society of Orthopedic Surgery and Traumatology 3rd International Clubfoot Congress, San Diego, California, Aug. 2002.

Cummings, RJ and Shanks, DE. A prospective randomized double-blind study of the usefulness of botox as an adjunct to serial manipulation and casting for congenital clubfeet. Pediatric Orthopedic Society of North America Annual Meeting. Ottawa, Canada May 12-15, 2005.

Karol, L. A., O'Brien, S. Mayberry S., Johnston, C., and Richards, B. Gait in patients with clubfeet: A comparison of physical therapy versus surgical release. (Pediatric Orthopedic Society of North America Annual Meeting), 72. 2003. Amelia Island, Florida, USA.

Kuo KN, Hennigan SP, Hastings ME. Long term results of clubfoot release, outcome study and gait analysis. Pediatric Orthopedic Society of North America 2003 Annual Meeting, Amelia Island, Florida, May 2-4, 2003.

Carruthers et al., "BOTOX use in the Mid and Lower Face and Neck", Seminars in Cutaneous Medicine and Surgery 20 (2001); 85-92.

Cummings et al., "Congenital Clubfoot", Journal of Bone and Joint Surgery 2002 (84); 290-308.

Dobbs et al, "Late Recurrence of Clubfoot Deformity: A 45-Year Followup", Clinical Orthopaedics and Related Research, 411 (2003): 188-192.

Jacks et al, "Clinical Usefulness of Botulinum Toxin in the Lower Extremity", Foot and Ankle Clinics 2004 (9): 339-348.

Roche et al, "Bilateral congenital idiopathic talipes equinovarus in twins", Eur. J. Orthop. Surg. Traumatol. 14 (2004) 201-202.

Scher, David M., "The Ponseti Method for Clubfoot Correction", Operative Techniques in Orthopaedics 15 (2005): 345-349.

BOTULINUM TOXIN IN TREATMENT OF CLUBFOOT RELAPSE

CROSS REFERENCE

This application is a nonprovisional utility application which claims priority to related provisional application No. 60/709,451, filed Aug. 19, 2005, the entire content of which application is incorporated herein by reference.

BACKGROUND OF THE INVENTION

1. Field of Invention

The present invention relates to the field of clubfoot therapy. More specifically, the invention relates to methods of therapy for clubfoot when a relapse has occurred.

2. Description of Related Art

Clubfoot, though predominantly a condition that occurs in isolation (idiopathic clubfoot), is also well-recognized in a variety of pre-existing conditions. Throughout most of the 20th century the mainstay of treatment of clubfoot has been surgical correction involving a variety of techniques (Carroll N C, McMurtry R, Leete S F. The pathoanatomy of congenital clubfoot. Orthop Clin North Am. 1978; 9:225-232; Carroll N C. Surgical technique for talipes equinovarus. Oper Tech Orthop. 1993; 3:115-120; Crawford A H, Marxen J L, Osterfeld D L. The Cincinnati incision; a comprehensive approach for surgical procedures of the foot and ankle in childhood. J Bone Joint Surg [Am]. 1982; 64:1355-1358; McKay D W. New concept of and approach to clubfoot treatment: section II. Correction of the clubfoot. J Pediatr Orthop. 1983; 3:10-21; Turco V J. Surgical correction of the resistant clubfoot: one-stage posteromedial release with internal fixation. A preliminary report. J Bone Joint Surg [Am]. 1971; 53:477-497). "Good" to "excellent" initial results have been reported in the range of 52% to 91% for these surgical methods (Herzenberg J E, Radler C R, Bor N. Ponseti versus traditional methods of casting for idiopathic clubfeet. J Pediatr Orthop. 2002; 22:517-521; Roye D P, Roye B D. Idiopathic congenital talipes equinovarus. J Am Acad Orthop Surg. 2002; 10:239-248). However, surgical interventions have associated reported complications in 11% to 50% of cases (Applington J P, Riddle C D. Avascular necrosis of the body of the talus after combined medial and lateral release of congenital clubfoot. South Med J. 1976; 69:1037-1038; Atar D, Lehman W B, Grant A D. Complications in clubfoot surgery. Orthop Rev. 1991; 20:233-239; Crawford A H, Gupta A K. Clubfoot controversies: complications and causes for failure. MOS Instr Course Lect. 1996; 45:339-346; Miller J H, Bernstein S M. The roentogenographic appearance of the corrected clubfoot. Foot Ankle. 1986; 6:177-183; Schlafly B, Butler J E, Sift S J. The appearance of the tarsal navicular after posteromedial release for clubfoot. Foot Ankle. 1985; 5:222-237). Often, complications are related to the Achilles tendon that may result in calcaneal deformity, from over-lengthening of the tendon or equinus from insufficient posterior release with or without under-lengthening of the Achilles tendon (Crawford A H, Gupta A K. Clubfoot controversies: complications and causes for failure. AAOS Instr Course Lect. 1996; 45:339-346). Postoperative gait analysis has shown abnormalities in ankle rocker formation and timing (Alkjaer T, Pedersen E N, Simonsen E B. Evaluation of the walking pattern in clubfoot patients who received early intensive treatment. J Pediatr Orthop. 2000; 20:642-647; Asperheim M S, Moore N, Carroll N C, et al. Evaluation of residual clubfoot deformities using gait analysis. J Pediatr Orthop B. 1995; 4:49-54; Hee H T, Lee E H, Lee G S. Gait and pedographic patterns of surgically treated clubfeet. J Foot Ankle Surg. 2001; 40:287-294; Karol L A, Concha M C, Johnston C E 2d. Gait analysis and muscle strength in children with surgically treated clubfeet. J Pediatr Orthop. 1997; 6:790-795; Karol L A, Mayberry S, O'Brien O, et al. Gait in patients with clubfeet: a comparison of physical therapy versus surgical release. Pediatric Orthopaedic Society of North America 2003 Annual Meeting, Amelia Island, Fla., May 2-4, 2003; Kuo K N, Hennigan S P, Hastings M E. Long term results of clubfoot release, outcome study and gait analysis. Pediatric Orthopaedic Society of North America 2003 Annual Meeting, Amelia Island, Fla., May 2-4, 2003; Otis J C, Bohne W H. Gait analysis in surgically treated clubfoot. J Pediatr Orthop. 1986; 6:162-164; Widhe T, Berggren I. Gait analysis and dynamic foot pressure in the assessment of the treated clubfoot. Foot Ankle Int. 1994; 15:186-190) and kinetic studies have revealed a significant decrease in power generation, with an average gastrosoleus muscle complex strength reduction of 27% after one Achilles tendon lengthening (Karol L A, Concha M C, Johnston C E 2d. Gait analysis and muscle strength in children with surgically treated clubfeet. J Pediatr Orthop. 1997; 6:790-795; Karol L A, Mayberry S, O'Brien O, et al. Gait in patients with clubfeet: a comparison of physical therapy versus surgical release. Pediatric Orthopaedic Society of North America 2003 Annual Meeting, Amelia Island, Fla., May 2-4, 2003; Kuo K N, Hennigan S P, Hastings M E. Long term results of clubfoot release, outcome study and gait analysis. Pediatric Orthopaedic Society of North America 2003 Annual Meeting, Amelia Island, Fla., May 2-4, 2003; Widhe T, Berggren I. Gait analysis and dynamic foot pressure in the assessment of the treated clubfoot. Foot Ankle Int. 1994; 15:186-190).

Ponseti published a protocol of serial manipulations and castings in 1980, reporting, at that time, that traditional surgery could be avoided in 89% of cases (Laaveg S J, Ponseti IV. Long-term results of treatment of congenital clubfoot. J Bone Joint Surg [Am]. 1980; 62:23-31) and, more recently, excellent functional and clinical outcomes in 78% of patients at 30-year follow-up (Cooper D M, Dietz F R. Treatment of idiopathic clubfeet: a thirty-year follow-up note. J Bone Joint Surg [Am]. 1995; 77:1477-1489). Unresolved hindfoot equinus, occurring in 70% to 90% of cases, was treated with percutaneous Achilles tenotomy. Other investigators have reported their experiences using the method described by Ponseti, quoting similarly favorable outcomes, albeit over a shorter follow-up (<3 years). Similarly, the physical therapy method also requires a significant rate of Achilles tenotomy (Bensahel H, Guillaume A, Desgrippes Y. Results of physical therapy for idiopathic clubfoot: a long-term follow-up. J Pediatr Orthop. 1990; 10:189-192). Bensahel et al reported a 26% surgical rate, which includes Achilles tenotomy (Bensahel H, Guillaume A, Desgrippes Y. Results of physical therapy for idiopathic clubfoot: a long-term follow-up. J Pediatr Orthop. 1990; 10:189-192) and Richards and Wilson (Richards B S, Wilson H. Non-operative clubfoot treatment using physical therapy. International Society of Orthopaedic Surgery and Traumatology 3rd International Clubfoot Congress, San Diego, Calif., August 2002) reported a 47% overall tenotomy rate.

Once correction of the clubfoot is achieved by the chosen method, maintenance is required. Maintenance involves 'boots and bars' or various orthoses, and has the prerequisite of correction, regardless of the methods and therapy involved in correction (surgical, non-surgical, pharmaceutical or a combination of these). A clubfoot that was corrected and goes on to redevelop features of a clubfoot is considered a relapse or recurrence of clubfoot. Recurrence is observed in about 30% of cases, with the highest incidence between the ages of 2 and 5.

A method of therapy for recurring or relapsing clubfoot that permits restoration of the normal foot position without requiring surgical intervention is desirable and needed. Novel pharmaceutical compositions comprising botulinum toxin or toxins are derived from the bacterium *Clostridium botulinum* and cause reversible muscle denervation by blocking the release of acetylcholine at the neuromuscular junction, leading to muscle relaxation. Botulinum toxin, specifically botulinum toxin A, is currently used in the treatment of cerebral palsy, poststroke spasticity, and other instances of inappropriate muscle contraction.

Reiter (Reiter, F, Danni, M., Lagalla, G., Ceravolo, G., Provinciali, L. 1998. Low dose botulinum toxin eith ankle taping for the treatment of spastic equinovarus foot after stroke. Arch Phys Med Rehabil 79:532-535) teaches use of BTX-A in combination with taping methods for treatment of spasticity following stroke. This treatment was administered to adult patients with previously normal foot function and was not directed to clubfoot treatment.

Delgado (Delgado et al. A preliminary report of the use of botulinum toxin type A in infants with clubfoot: four case studies. *Journal of Pediatric Orthopedics*. 2000; 20(4):533-8) reported application of a nonsurgical intervention for clubfoot therapy with the initial management involving physical therapy. A group of infant patients under the age of 1 year with clubfoot deformity were treated with BTX-A to resolve the abnormal foot posture. Several of these patients' conditions were dystonic in nature due to underlying disorders, and could not be considered 'idiopathic' in nature. Delgado's methods involved injection into both the gastrocnemius and the posterior tibial muscles, and dosages varied from 6-11 IU/kg. Delgado's methods used multiple muscle sites at multiple irregular intervals (on average three separate injection events) for all patients. In addition, 50% of the patients required additional surgery after 1 year of age. No discussion of relapse or therapeutic approaches to relapse was addressed.

Cummings (Cummings, R J and Shanks, D E. A prospective randomized double-blind study of the usefulness of botox as an adjunct to serial manipulation and casting for congenital clubfeet. Pediatric Orthopaedic Society of North America Annual Meeting. Ottawa, Canada May 12-15, 2005) presented a study suggesting that use of Botox™ in combination with the Ponseti methods was not a successful treatment for clubfoot.

There are a wide variety of approaches to therapy of spastic muscle disorders, particularly clubfoot in infants. Given the range of casting and manipulation methods, and the range in patient classification, dosages and compositions of botulinum toxin used, the method may have promise, however very specific diagnoses and treatment methodologies may be required. The conclusions of Cummings (Cummings, R J and Shanks, D E. A prospective randomized double-blind study of the usefulness of botox as an adjunct to serial manipulation and casting for congenital clubfeet. Pediatric Orthopaedic Society of North America Annual Meeting. Ottawa, Canada May 12-15, 2005) suggest that the details of the methods used, including the injected sites, matter significantly. Merely 'mashing together' various treatment regimens as may be suggested by some studies will not be successful in both primary treatment of idiopathic clubfoot and prevention of relapse.

In situations where the clubfoot deformity relapses, surgical correction is currently the standard of care in almost every case. Surgical correction carries with it additional complications and, if surgical methods can be avoided, scarring, tissue weakness and overcorrection are also avoided, and in severe cases, multiple correction attempts may be made. Surgical correction of clubfoot is limited—tenotomy is strongly recommended to not be performed more than twice as it causes causing structural weakness in the tendon having adverse effects on recovery and gait. Non-invasive methods are better accepted by parents and caregivers, and are less distressing on the patient.

SUMMARY OF THE INVENTION

In accordance with one aspect of the invention, there is provided a method of reducing supination in a relapsed clubfoot-affected foot of a patient, the method comprising injecting a medicament comprising a neuromuscular paralytic agent into at least two sites of a tibialis posterior muscle adjoining the clubfoot-affected foot.

In accordance with another aspect of the invention, there is provided a method of reducing equinus in a relapsed clubfoot-affected foot of a patient, the method comprising, injecting a medicament comprising a neuromuscular paralytic agent into at least four sites of a gastrosoleus muscle complex adjoining the clubfoot-affected foot.

In accordance with another aspect of the invention, there is provided a method of reducing adductus in a relapsed clubfoot-affected foot of a patient, the method comprising, injecting a medicament comprising a neuromuscular paralytic agent into at least 1 site of an abductor hallucis muscle adjoining the clubfoot-affected foot.

The tibialis posterior or the abductor hallucis may be first identified by use of a muscle stimulator.

The neuromuscular paralytic agent may be an acetylcholine antagonist, such as a botulinum toxin, more specifically botulinum toxin A. A medicament comprising such a toxin may include Botox™ and Myobloc™.

Following administration of the neuromuscular paralytic agent, the clubfoot-affected foot is casted.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention.

DETAILED DESCRIPTION

Figure 1:
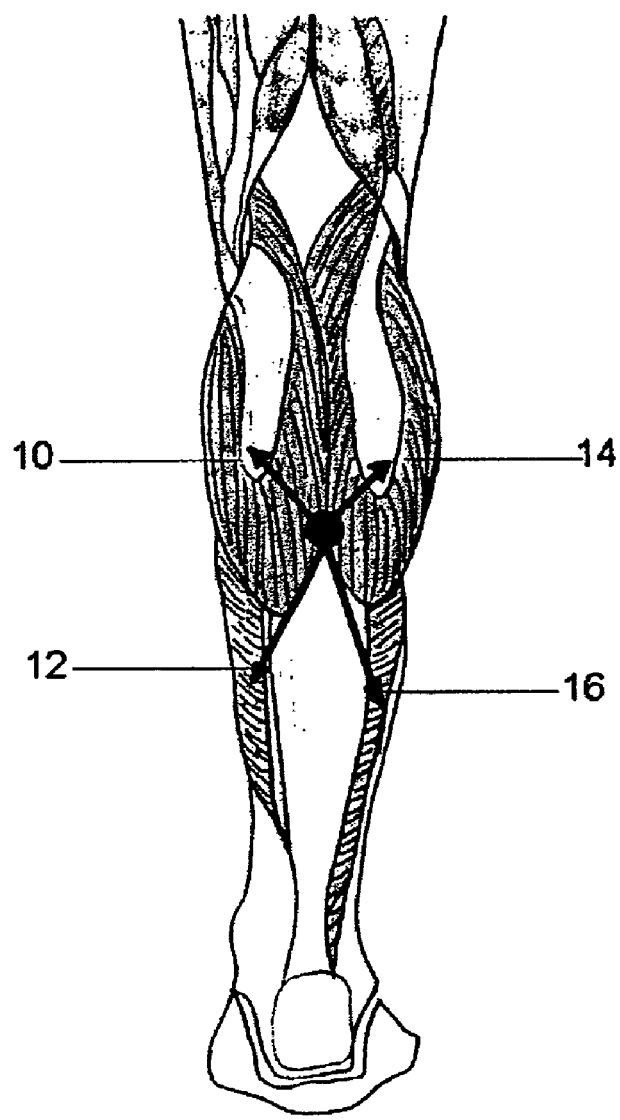
FIG. 1 is a graphical illustration of the posterior view of the lower leg, showing the BTX-A injection pattern.
Figure 2:
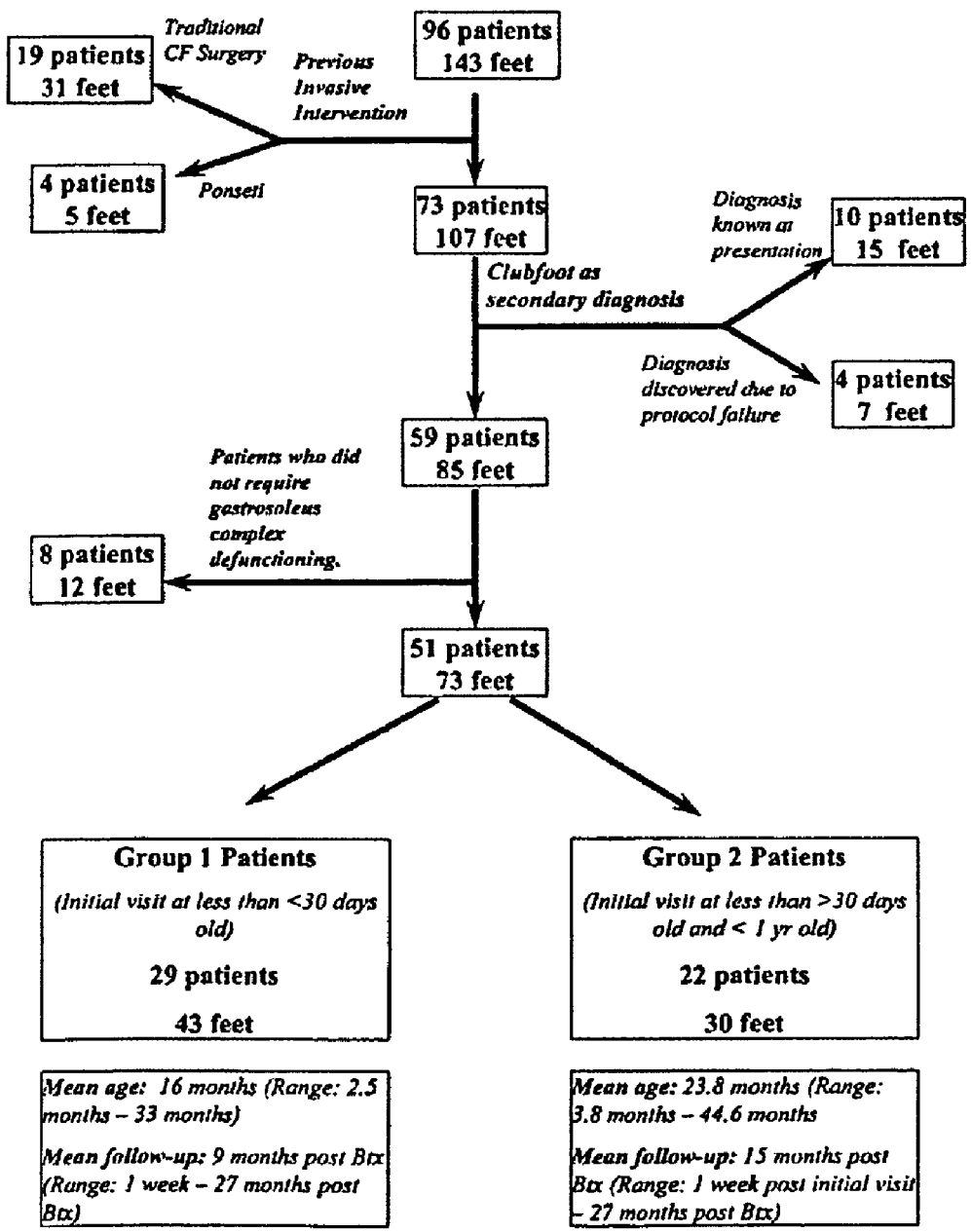
FIG. 2 is a flow chart depicting the selection and treatments of the trial patients.
Figure 3:
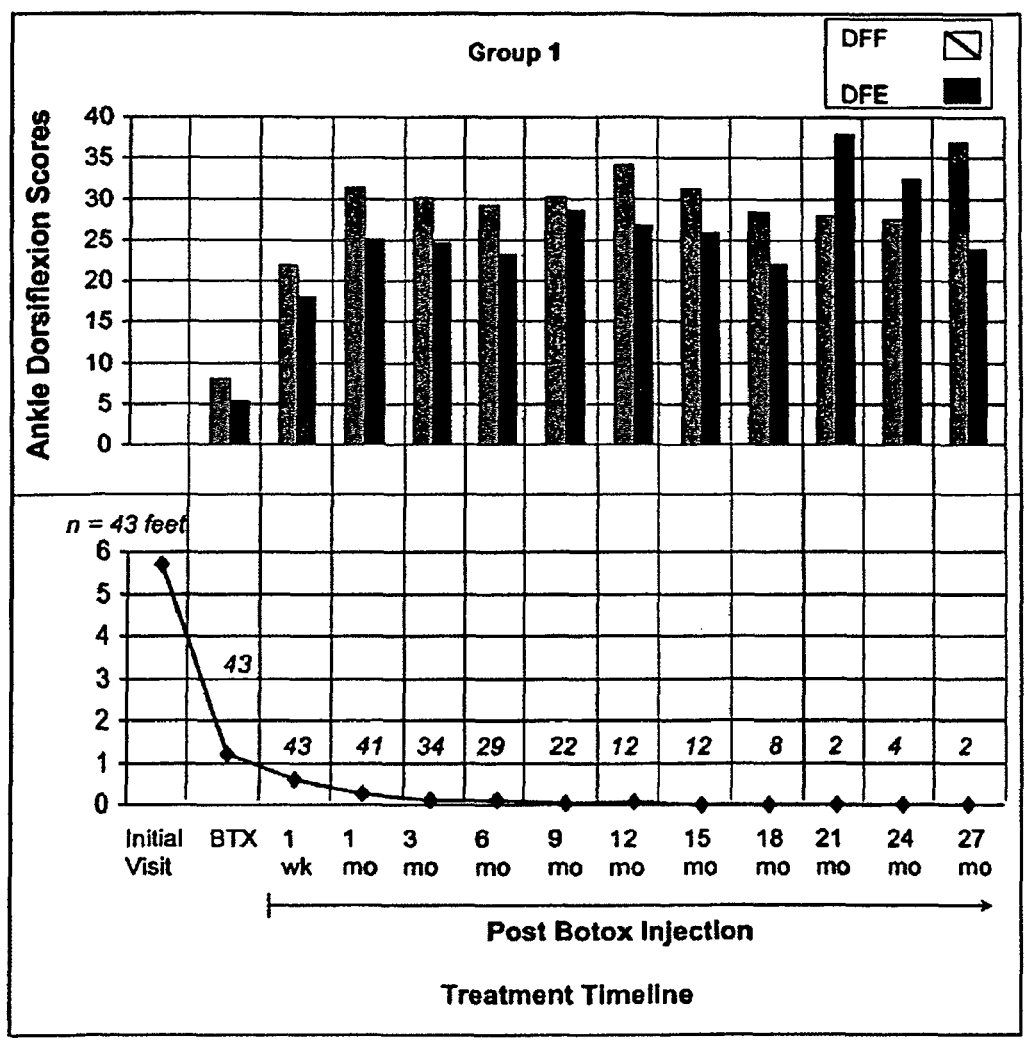
FIG. 3 shows superimposed graphs representing outcome scores for group 1 patients. Bar graphs show dorsiflexion scores for both the knee in flexion (DFF) and in extension (DFE) and line graphs below show Pirani scores. Treatment timeline from initial visit to 27 months after BTX-A injection is shown on the horizontal axis.
Figure 4:
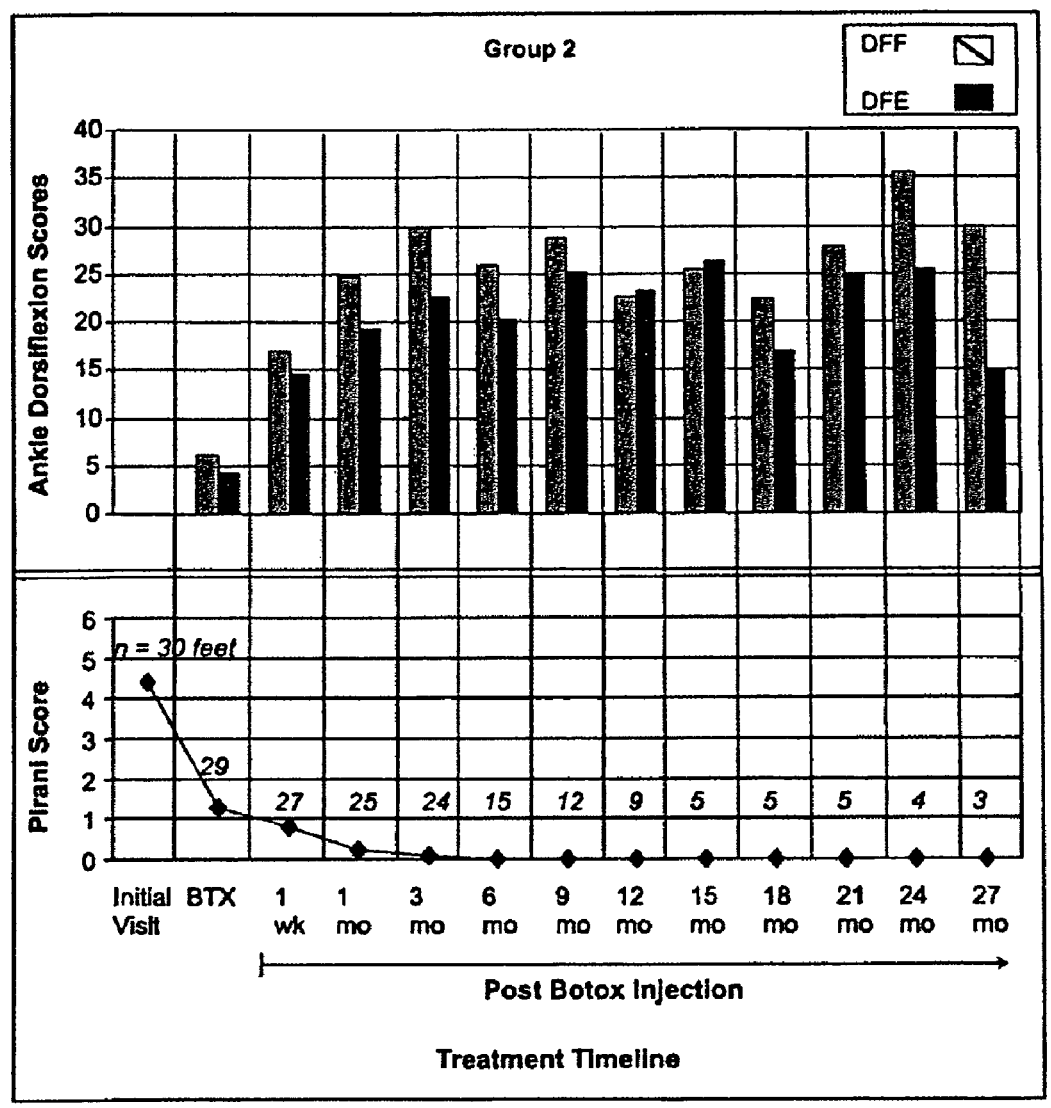
FIG. 4 shows superimposed graphs representing outcome scores for group 2 patients. Bar graphs show dorsiflexion scores for both the knee in flexion (DFF) and in extension (DFE) and line graphs below show Pirani scores. Treatment timeline from initial visit to 27 months after BTX-A injection is shown on the horizontal axis.

Any terms not directly defined herein shall be understood to have the meanings commonly associated with them as understood within the art of the invention. As employed throughout the specification, the following terms, unless otherwise indicated, shall be understood to have the following meanings.

"Clubfoot" or "clubfoot deformity" as used herein refers to the presence of a foot of a human that cannot be corrected with manipulation to a normal flexible forefoot, midfoot, and hindfoot position. Clubfoot may occur in one or both feet of an individual. Clubfoot may occur as a single isolated defect with no underlying cause, or may occur in conjunction with one or more coexisting disorders.

"Idiopathic clubfoot" or "idiopathic clubfoot deformity" as used herein refers to clubfoot with no coexisting disorders.

"Non-idiopathic clubfoot" or "non-idiopathic clubfoot deformity" as used herein refers to clubfoot in the presence of a coexisting disorder. Such coexisting disorders may include myelomenginocoele, arthrgryposis, migration abnormalities of the brain, cerebral palsy, positional deformitie, neurological disorders, spina bifida, trichorhinophalangeal syndrome or other unspecified genetic syndromes resulting in the presence of clubfoot in a patient.

"Normal foot posture" or "normal posture of the foot" as used herein refers to a hindfoot that is in neutral to valgus and plantigrade, a midfoot which is neutral with mild limits of supination and pronation, and a forefoot that is neutral with the heel bisector at the ⅔ space plus or minus 1 heel bisector.

"Triceps surae complex", as used herein, refers collectively to the gastrocnemius and soleus muscles of the lower leg. An alternative term may be gastrosoleus or gastrocsoleus, also referring collectively to the gastrocnemius and soleus muscles of the lower leg.

"Percutaneous Achilles tenotomy", as used herein, refers to a surgical procedure to lengthen the Achilles tendon, where under sterile conditions, a surgical blade is inserted deep into the Achilles tendon near the insertion into the calcaneus and the tendon incompletely transected. A full tenotomy transects the tendon and releases it, while an Achilles lengthening procedure actually gives length to tendon but reattaches the two ends together, thereby allowing control in the desired extent of lengthening.

A "Pirani score" as used herein refers to a scoring system for assessment of clubfoot (Pirani S, Outerbridge H, Moran M, Sawatsky B J. A method of evaluating the virgin clubfoot with substantial interobserver reliability. Pediatric Orthopaedic Society of North America 1995 Annual Meeting, Miami, Fla., May 1995; Flynn J M et al. An independent assessment of two clubfoot-classification systems. *Journal of Pediatric Orthopedics*. 18(3):323-7, 1998). The Pirani score used comprised three measures for the midfoot and three for the hindfoot (each scored as 0, 0.5, or 1.0, for a total score ranging from 0 to 6, the higher score reflecting the more severe deformity). An alternate classification schema for clubfoot is that of Dimeglio and Bensahel ("Dimeglio system") (Dimeglio A, Bensahel H, Souchet Ph, Mazeau P, Bonnet F. Classification of clubfoot. *Journal of Pediatric Orthopaedics (Br)* 1995; 4:129-136). The Dimeglio system characterizes the severity of clubfoot deformity into four grades, based on varus and equinus in the sagittal plane, derotation of the calcaneopedal block, and position of the forefoot relative to the hindfoot in the horizontal plane. A Grade 1 foot is mild (soft-soft); a Grade 2 foot is moderate (soft to stiff); a Grade 3 foot is severe (stiff to soft) and a Grade 4 foot is very severe, pseudoarthrogryotic feet (stiff-stiff). The efficacy of correction of clubfoot may be assessed by the degree of ankle dorsiflexsion, as assessed with the knee in both extension and flexion.

Clubfoot correction resulting from treatment refers to a response to this treatment. An alternate term is 'clubfoot management'. The corrected clubfoot deformity is measured by the amount of motion achieved by a patient. This is based on clubfoot treatment decisions, specifically, if the patient is able to fit into corrective bracing (achieve ankle dorsiflexion of 10 degrees or greater) which is an indicator of correction of the clubfoot.

A patient relapse, as used herein refers a loss of dorsiflexion (with knee in flexion <5 degrees and/or with knee in extension <0 degrees), in a patient currently receiving or having previously received therapeutic intervention for clubfoot.

"Equinus", or "talipes equinus", as used herein, refers to a deformity of the foot in which the sole is flexed below neutral or in the plantarflexed range (specifically ankle dorsiflexion is less than 0 degrees). Walking is done on the toes without touching the heel to the ground. 'Toe walking' is an alternate term to describe this altered foot position's resulting gait.

"Hindfoot stall", as used herein, refers to a state wherein the forefoot may be abducted to 60 degrees with persistent hindfoot equinus present, or if the lateral radiograph of the foot demonstrates a downgoing calcaneus and/or talocalcaneal parallelism.

An 'antagonist', as used herein, refers to a chemical entity that acts to reduce the physiological activity of another chemical entity, for example by combining with and blocking the receptor of the endogenous chemical entity.

A "chemical entity", as used herein refers to small organic or inorganic molecules with distinct molecular composition made synthetically, found in nature, or of partial synthetic origin. Included in this group are nucleotides, nucleic acids, amino acids, peptides, proteins, or complexes comprising at least one of these entities, such as a chromosome.

A "medicament", as used herein, refers to a chemical entity capable of producing an effect that may be administered to a patient or test subject. The effect may be chemical, biological or physical, and the patient or test subject may be human, or a non-human animal, such as a rodent or transgenic mouse. The medicament may be comprised of the effective chemical entity alone or in combination with a pharmaceutically acceptable excipient.

A pharmaceutically acceptable excipient includes any and all solvents, dispersion media, coatings, antibacterial, antimicrobial or antifungal agents, isotonic and absorption delaying agents, and the like that are physiologically compatable. The excipient may be suitable for intravenous, intraperitoneal, intramuscular, intrathecal or oral administration. The excipient may include sterile aqueous solutions or dispersions for extemporaneous preparation of sterile injectable solutions or dispersion. Use of such media for preparation of medicaments is known in the art.

A pharmacologically effective amount of a medicament as used herein refers to using an amount of a medicament present in such a concentration to result in a therapeutic level of drug delivered over the term that the drug is used. This may be dependent on mode of delivery, time period of the dosage, age, weight, general health, sex and diet of the subject receiving the medicament.

The medicaments of the present invention may be formulated for administration by any of various routes. The medicaments may include an excipient in combination with the effective chemical entity, and may be in the form of, for example, tablets, capsules, powders, granules, lozenges, pill, suppositories, liquid or gel preparations, or an injectable formulation, suitable for subcutaneous, intramuscular, intravenous, intraperitoneal, intra-arterial or other modes of injectable delivery. Medicaments may be formulated for parenteral administration in a sterile medium. The medicament may be dissolved or suspended in the medium. Medicaments may be formulated for a subdermal implant in the form of a pellet, rod or granule. The implant or implants may be inserted subcutaneously by open surgery or by use of a trochar and cannula under local anaesthesia. The implant may be periodically replaced or removed altogether. Medicaments may also be formulated for transdermal administration using a patch. The patch is applied to a shaven area of the skin of the patient while the medicament is desired for administration, and removed when no longer needed.

A "neuromuscular paralytic agent", as used herein, refers to an acetylcholine antagonist, an acetylcholine release inhibitor or a cholinergic release inhibitor. Neuromuscular paralytic agents generally exert their effect by blocking acetylcholine release from a presynaptic terminal of a nerve ending at a neuromuscular junction. Administration of a neuromuscular paralytic agent in a medicament may result in a degree of paralysis of the muscle at the site of administration. The paralysis may be reversible or irreversible.

"Botulinum toxin", as used herein, refers to a neuromuscular paralytic agent normally produced by the *Clostridium botulinum* bacteria. Botulinum toxin A, botulinum type A toxin or botulinum toxin type A may be abbreviated as BTX-A. Botulinum toxin B, botulinum type B toxin or botulinum toxin type B may be abbreviated as BTX-B. Botox™ (Allergan), also referenced as Oculinum™ or Dysport™, is a commercially produced medicament comprising BTX-A. Myobloc™ or Neurobloc™ (Solstice Neurosciences) is a commercially produced medicament comprising BTX-B. Other botulinum toxins include botulinum toxin C, botulinum toxin D, botulinum toxin E, botulinum toxin F and botulinum toxin G—these may be administered in the form of a medicament comprising such toxins.

Physical therapy approaches for the treatment of clubfoot in infants vary. The most commonly used and peer-reviewed method is that of Bensahel and Dimeglio (Bensahel H, Guillaume A, Desgrippes Y. Results of physical therapy for idiopathic clubfoot: a longterm follow up. *Journal of Pediatric Orthopaedics* 1990; 10:189-192; Seringe R, Atia R. Idiopathic congenital clubfoot. Results of functional treatment. *Revue de Chirurgie Orthopedique et Reparatrice de l'Appareil Moteur* 1990; 76:490-501; Souchet P, Bensahel H, Themar-Noel C, Pennecot G, Csukonyi Z. Functional treatment of clubfoot: A new series of 350 idiopathic clubfeet with long-term follow-up. *Journal of Pediatric Orthopaedics* (*Br*) 2004; 13:189-196). The Ponseti method involves a set methodology of manipulations and casting of the foot and is an intensive and involved method, requiring significant caregiver compliance and participation. The Ponseti method generally requires that all components of the clubfoot be corrected simultaneously, except for equinus, which is corrected last. The cavus is corrected together with the adduction by supinating and abducting the forefoot in proper alignment with the hindfoot. With the arch well moulded and the foot in slight supiation, the entire foot can be gently and gradually abducted under the talus, which is secured against toration in the ankle mortise by applying counterpressure (with the thumb of the therapist) against the lateral part of the talus head. Heel varus is corrected when the entire foot is fully abducted. Finally, equinus is corrected by performing an Achilles tenotomy in 80% of cases. Percutaneous Achilles tenotomy is the current approach in the art, and while simple to perform technically, may lead to immediate complications causing neurovascular injury. Further, it may lead to future complications of such as skin scarring and deep tissue fibrosis resulting in reduced ankle joint range of motion and power push off, affecting the gait. Additional complications are introduced if the clubfoot deformity relapses, especially if an initial tenotomy has been performed.

Relapse occurs in about 30% of cases, and usually after the patient has become an active child and in some cases ready to enter school. The most common deformities in relapse are supination, equinus and adductus.

The deforming force causing the supination is in part attributed to the tibialis posterior muscle. In the untreated club foot one of the major deforming forces is the tibialis posterior and its lengthening is one of the principal steps performed in a clubfoot release (Carroll N C. Surgical technique for talipes equinovarus. Oper Tech Orthop. 1993; 3:115-120; Crawford A H, Marxen J L, Osterfeld D L. The Cincinnati incision; a comprehensive approach for surgical procedures of the foot and ankle in childhood. J Bone Joint Surg [Am]. 1982; 64:1355-1358; McKay DW. New concept of and approach to clubfoot treatment: section II. Correction of the clubfoot. J Pediatr Orthop. 1983; 3:10-21; Turco VJ. Surgical correction of the resistant clubfoot: one-stage posteromedial release with internal fixation. A preliminary report. J Bone Joint Surg [Am]. 1971; 53:477-497). During stance, tibialis posterior contracts as part of the intrinsic foot muscle control. The tibialis posterior contracts specifically at initial contact with the ground causing a supination torque. The peak action of the tibialis posterior is related to subtalar deceleration and stability. It therefore presents as supination of the midfoot in stance and can contribute to an associated hindfoot varus. In swing phase, the tibialis posterior does not normally contract, however if overactive it will act alongside the anterior tibial muscles, having the net effect of both supination and equinus during leg swing.

The equinus deformity in the recurrences is mostly attributed to the Achilles tendon and its associated gastrosoleus muscle complex. Here too, if the complex is overactive, equinus will be seen both in the stance and swing phases of gait as it normally fires in both.

Recurrence of the forefoot adductus is also common in relapse. The abductor hallucis muscle is the primary deforming force causing adduction of the forefoot. In the swing phase of the affected patient's gait, exaggeration of forefoot internal progression is the result in part of abductor hallucis, and its overactivity can persist in stance causing an increase in the heel bisector.

The heel bisector score described by Bleck refers to the reference line passing through the longitudinal axis of the heel along the plantar surface of the foot (Bleck, E. Metatarsus adductus: Classification and relationship to outcomes of treatment. *Journal of Pediatric Orthopaedics* 1983; 3:2-9). A normal foot is characterized by the line passing through the $2^{nd}$ toe (a heel bisector score of 2), mild forefoot adductus by a heel bisector of 3, moderate by a heel bisector of 4, and severe by a heel bisector of 5.

For relapse of clubfoot with supination, the standard of treatment is a tibialis anterior transfer. In this surgical procedure, the tibialis anterior muscle is transferred from its original insertion in the $1^{st}$ metatarsal into the $3^{rd}$ (lateral) cuneiform (Garceau, G. Anterior tibial tendon transfer for recurrent clubfoot. *Clinical Orthopaedics and Related Research* 1972; 84:61.5; Garcaeu, G, Palmer, R. Transfer of the anterior tibial tendon for recurrent clubfoot: A long-term follow-up. *Journal of Bone and Joint Surgery* 1967; 49:207-31). This transfer addresses the supination deformity of the foot by balancing out the action on the foot imposed by tibialis posterior. By moving the tibialis anterior onto the lateral dorsum of the foot, the activity of the tibialis posterior is counteracted during the swing phase of the patient's gait, allowing the foot to swing through in a neutral position. The tibialis anterior has no deforming force in a clubfoot however, and by transferring it surgically, it does not directly address the problem—the pathologic forces incurred by tibialis posterior on the relapsed foot. The tibialis posterior is predominantly a stance phase muscle and cannot be balanced out is stance as tibialis anterior is silent in stance. The tibialis posterior, therefore needs to be treated directly to effect the appropriate changes, rather than surgically treating a 'surrogate' muscle—the tibialis anterior.

For treating relapse of clubfoot with an equinus contracture, additional Achilles lengthening is required and an Achilles tenotomy or formal open lengthening is the standard of care. Depending on the progress of the initial clubfoot management, this may be at least the second Achilles tenotomy or lengthening procedure performed on the patient. The deformation induced by the muscle is directly addressed by tenotomy, but the surgery is accompanied by the risks inherent with the procedure, including general anaesthesia. Furthermore, each time the Achilles tendon is sectioned, weakness is introduced resulting in decreased power of push-off when ambulating, and diminished range of ankle motion (Karol L A, Concha M C, Johnston C. E. 2nd. Gait analysis and muscle strength in children with surgically treated clubfeet. *Journal of Pediatric Orthopaedics* 1997; 6:790-795; Karol, L. A., O'Brien, S. Mayberry S., Johnston, C., and Richards, B. Gait in patients with clubfeet: A comparison of physical therapy versus surgical release. (Paediatric Orthopedic Society of North America Annual Meeting), 72. 2003. Amelia Island, Fla., USA; Kuo K N, Hennigan S P and Hastings M E. Long term results of clubfoot release, outcome study and gait analysis. Pediatric Orthopaedic Society of North America 2003 Annual Meeting, Amelia Island, Fla., May 2-4, 2003; Widhe T, Berggren I. Gait analysis and dynamic foot pressure in the assessment of the treated clubfoot. *Foot Ankle Int* 1994; 15:186-190).

The standard of care for relapse of clubfoot with forefoot adductus is a double tarsal osteotomy or "flip flop" osteotomy, usually performed once the child is over 4 years of age and ideally 6 years or older (Morrissy R T, Weinstein S Le. *Lovell and Winter's Pediatric Orthopaedics*. Philadelphia, Pa., USA: Lippincott-Raven, 1996). This procedure involves dividing the medial cuneiform in half and taking a laterally based wedge out of the cuboid and inserting this wedge into the divided medial cuneiform thereby forcing the foot from adductus to abductus, based on the size of the wedge. Metatarsus adductus, independent of clubfoot, may also treated initially with manipulation and casting, but may require surgical intervention such as tarsal osteotomy if unsuccessful, or if a relapse occurs.

Each of these relapse or recurrence events do not necessarily occur in isolation, and frequently are concurrent, however each deformity must be addressed individually. Injection of a neuromuscular paralytic agent, for example a botulinum toxin, into the effector muscle in each case will circumvent the need for surgical intervention. Supination may be addressed by specifically treating the tibialis posterior. Equinus may be addressed by specifically treating the gastrosoleus complex, while forefoot adductus may be addressed by specifically treating the abductor hallucis muscle, weakening it sufficiently to address the adductus. Manipulations and casting methods accompany all of these interventions to obtain correction after relapse, and further bracing methods used for maintenance of the corrected foot posture.

Neuromuscular paralytic agents, for example botulinum toxin type A (BTX-A, Botox™) cause partial reversible muscle paralysis (Brin M F, ed. Spasticity: etiology, evaluation, management, and the role of botulinum toxin A. Muscle Nerve. 1997; 20(Supp 6):61-91; Eames N W, Baker R, Hill N, et al. The effect of botulinum A toxin on gastrocnemius length: magnitude and duration of effect. Dev Med Child Neurol. 1999; 41:226-232; Juzans P, Comella J X, Molgo J, et al. Nerve terminal sprouting in botulinum A-treated mouse levator auris longus muscle. Neuromuscul Disord. 1996; 6:177-185). BTX-A acts by blocking acetylcholine release from the presynaptic terminal of peripheral nerve endings at the neuromuscular junction. Intramuscular injection of BTX-A has been shown to lead to partial paralysis of the respective muscle and has been shown to be effective in a number of disorders (Bang M S, Chung S G, Kim S B, et al. Change of dynamic gastrocnemius and soleus muscle length after block of spastic muscle in cerebral palsy. Am J Phys Med Rehabil. 2002; 81:760-764; Brin M F, ed. Spasticity: etiology, evaluation, management, and the role of botulinum toxin A. Muscle Nerve. 1997; 20(Supp 6):61-91; Eames N W, Baker R, Hill N, et al. The effect of botulinum A toxin on gastrocnemius length: magnitude and duration of effect. Dev Med Child Neurol. 1999; 41:226-232; Juzans P, Comella J X, Molgo J, et al. Nerve terminal sprouting in botulinum A-treated mouse levator auris longus muscle. Neuromuscul Disord. 1996; 6:177-185; Klein A W. Complications and adverse reactions with the use of botulinum toxin. Semin Cutan Med Surg. 2001; 20:109-120; Scott A B. Botulinum A injection of eye muscles to correct strabismus. Trans Am Ophthalmol Soc. 1981; 79:734-770) and safe across all ages studied (2 days old to adults) (Brin M F, ed. Spasticity: etiology, evaluation, management, and the role of botulinum toxin A. Muscle Nerve. 1997; 20(Supp 6):61-91; Edgar T S. Clinical utility of botulinum toxin in the treatment of cerebral palsy: comprehensive review. J Child Neurol. 2001; 16:37-46; McNeer K W, Tucker M G, Spencer R F. Management of essential infantile esotropia with botulinum toxin A: review and recommendations. J Pediatr Ophthalmol Strabismus. 2000; 37:63-67). Side effects are rare and transient (Bakheit A M, Severa S, Cosgrove A, et al. Safety profile and efficacy of Botulinum toxin A (Dysport) in children with muscle spasticity. Dev Med Child Neurol. 2001; 43:234-238; Juzans P, Comella J X, Molgo J, et al. Nerve terminal sprouting in botulinum A-treated mouse levator auris longus muscle. Neuromuscul Disord. 1996; 6:177-185; Klein A W. Complications and adverse reactions with the use of botulinum toxin. Semin Cutan Med Surg. 2001; 20:109-120) and repeated doses may be given if necessary without concern of inducing any long-term complications (Brin M F, ed. Spasticity: etiology, evaluation, management, and the role of botulinum toxin A. Muscle Nerve. 1997; 20(Supp 6):61-91; Mooney J F, Koman L A, Smith B P. Pharmacologic management of spasticity in cerebral palsy. J Pediatr Orthop. 2003; 23:679-686).

Methods

Identification of Relapse

A clubfoot relapse is identified by assessment of equinus, supination and adductus in a patient previously or currently treated for clubfoot. A relapse of equinus is determined based on the dorsiflexion scores, a relapse of supination is based on heel and midfoot varus and supination respectively, and a relapse of adductus is determined on the basis of heel bisector. A general indication of relapse is the ability to place the affected foot or feet of the patient into boots and bars or orthoses. If any of these 3 relapses exist bracing becomes intolerable and therefore correction is, or has been, lost.

Treatment of Clubfoot Relapse with Supination

The tibialis posterior of the clubfoot-affected limb is injected with Botox™ while the patient is sedated or under a general anaesthetic stimulator is used to identify the tibialis posterior in advance of injection. A minimum of two sites of the tibialis posterior are injected and the muscle is massaged for about 20 seconds following injection. Above-knee manipulation in the maximally abducted and externally rotated position tolerated by the patient is performed, followed by above knee casting. The patient is permitted to fully weight bear on the cast ad libidum. The cast is changed 2-3 weeks later and a below knee manipulation and casting performed with maximum tolerable correction. 2-3 weeks following the second casting, the patient enters a maintenance bracing program full time for 3 months and then only at night (about 12 hours per day) until the brace is outgrown. Daytime shoe wear is then prescribed.

Treatment of Clubfoot Relapse with Equinus

The gastrosoleus muscle complex of the clubfoot-affected limb is injected with Botox™ while the patient is sedated or under a general anaesthetic, if the tibialis posterior and/or abductor hallucis are treated simultaneously. If the gastrosoleus muscle complex is treated in isolation, the procedure may be performed in an outpatient setting. Injection of the gastrosoleus muscle complex is performed in a stellate pattern at a minimum of 4 sites, including the distal soleus of the affected leg. The muscle is massaged for about 20 seconds following injection and a below-knee cast (if the gastrosoleus muscle complex is treated in isolation, otherwise an above-knee cast is used) is applied to the clubfoot-affected leg in the maximum tolerated dorsiflexion posture. The patient is permitted to fully weight bear on the cast ad libitum. The cast is changed 2-3 weeks later and a second cast applied to the affected leg in maximal dorsiflexion. 2-3 weeks following the second casting, the patient enters a maintenance bracing program full time for 3 months and then only at night until the brace is outgrown. Daytime shoe wear is then prescribed.

Treatment of Clubfoot Relapse with Adductus

The abductor hallucis of the clubfoot-affected limb is injected with Botox™ while the patient is sedated or under a general anaesthetic. A muscle stimulator is used to identify the abductor hallucis muscle in advance of injection. Up to 3 sites are injected and the muscle is massaged for 20 seconds following each injection and a below-knee cast (if the abductor hallucis is treated alone or in conjunction with the gastrosoleus muscle complex, otherwise an above-knee cast is used) is applied to the clubfoot-affected leg in the maximum tolerable corrected foot posture. The patient is permitted to fully weight bear on the cast ad libitum. The cast is changed 2-3 weeks later and a second cast applied to the affected leg in maximum tolerated corrected foot posture. 2-3 weeks following the second casting, the patient enters a maintenance bracing program full time for 3 months and then only at night until the brace is outgrown. Daytime shoe wear is then prescribed.

Treatment of Metatarsus Adductus Relapse

A relapse of metatarsus adductus, independent of clubfoot may also be treated in a similar manner to that of adductus relapse in clubfoot.

For all treatments, a dosage range from about 10 IU/kg to about 20 IU/kg may be used, divided between the required injection sites. Minimal dosing at an individual site may comprise:

Gastrocnemius 3-6 IU/kg; soleus 2-3 IU/kg
Tibialis posterior 1-2 IU/kg
Abductor hallucis 1-2 IU/kg Bracing Protocol As required, Denis Browne bar and corrective shoes (boots and bars) were fitted to the patient as described in the art. Alternatively, custom-fitted knee-ankle-foot orthoses (KAFO) were required in a few patients due to intolerance of the boots and bars.

EXAMPLES

TABLE 1

Results of treating Gastrosoleus only

| Number of Patients | 7 |
|---|---|
| Patient Outcomes | Ankle Range of Motion:<br>DFF (ankle dorsiflexion with knee in flexion)<br>DFE (ankle dorsiflexion with knee in extension) |

| | Pre-Injection | | Post-Injection 8 weeks post | |
|---|---|---|---|---|
| | Right Foot | Left Foot | Right Foot | Left Foot |
| Pilot Results | Mean DFF: 3<br>Mean DFE: 1 | Mean DFF: 5<br>Mean DFE: 2 | Mean DFF: 18<br>Mean DFE: 11 | Mean DFF: 22<br>Mean DFE: 17 |

TABLE 2

Results of treating gastrosoleus and tibialis posterior simultaneously

| Number of Patients | 13 |
|---|---|
| Patient Outcomes | 1. Ankle Range of Motion:<br>    DFF (ankle dorsiflexion with knee in flexion)<br>    DFE (ankle dorsiflexion with knee in extension)<br>2. Clinical observation of hindfoot position<br>3. Pedobarography |

Pilot Results

| | Pre-Injection | | Post-Injection 8 weeks post | |
|---|---|---|---|---|
| | Right Foot | Left Foot | Right Foot | Left Foot |
| 1. Ankle Range of Motion | Mean DFF: 9<br>Mean DFE: 5 | Mean DFF: 7<br>Mean DFE: 5 | Mean DFF: 9<br>Mean DFE: 5 | Mean DFF: 19<br>Mean DFE: 17 |

| 2. Clinical observation of hindfoot position | The influence of the tibialis posterior muscle is seen in the hindfoot and the midfoot during standing (static phase) and walking (dynamic phase). The characteristics of the foot that are observed clinically are as follows:<br>Static Phase:    Hindfoot in varus?<br>                  Midfoot in supination?<br>Dynamic Phase:  Hindfoot (heel) striking at initial contact?<br>                  Midfoot in supination at initial contact?<br>                  Hindfoot in varus during swing?<br>                  Midfoot in supination during swing?<br>Clinical observation of the hindfoot and midfoot was synthesized as dichotomous data (yes/no) for each patient. Pre-injection, patients showed hindfoot varus and |

TABLE 2-continued

Results of treating gastrosoleus and tibialis posterior simultaneously

|  |  |
|---|---|
|  | midfoot supination during the static phase. There was no hindfoot strike and the midfoot was in supination at hindfoot strike during initial contact of the dynamic phase. During swing in the dynamic phase, the hindfoot was in varus and midfoot in supination for patients. Such clinical features were indications for Botox injection in the tibialis-posterior muscle.<br>Post-injection, 1 of 13 patients (1 of 22 injected clubfeet) converted and showed response to the Botox. |
| 3. Pedobarography | Pedobarography data were not synthesized for purposes of this patent application. |

TABLE 3

Results of treating abducutor hallucis only

| Number of Patients |  |  | 4 |  |  |  |
|---|---|---|---|---|---|---|
| Patient Outcomes |  |  | Heel Bisector Scores |  |  |  |
|  | Pre-Injection |  | Post-Injection 8 weeks post |  |  |  |
| Pilot Results | Right Foot | Left Foot | Right Foot | Avg Change | Left Foot | Avg Change |
|  | Pt 1: ¾ | Pt 1: ¾ | Pt 1: 3 | ½ | Pt 1: ¾ | 0 |
|  | Pt 2: ⅘ | Pt 2: ⅘ | Pt 2: 3 | 1½ | Pt 2: 3 | 1½ |
|  | Pt 3: ¾ | Pt 3: ¾ | Pt 3: 2 | 1½ | Pt 3: 2 | 1½ |
|  | Pt 4: ¾ | Pt 4: ¾ | Pt 4: ¾ | 0 | Pt 4: 1 | 2½ |

Six out of 8 patients showed an average improvement of 1.125 heel bisectors.

While specific embodiments of the invention have been described and illustrated, such embodiments should be considered illustrative of the invention only and not as limiting the invention as construed in accordance with the accompanying claims.

Based on the foregoing, it will be appreciated that the present invention provides the following advances over the art:

A method of reducing supination in a relapsed clubfoot-affected foot of a patient, the method comprising;
   injecting a medicament comprising a neuromuscular paralytic agent into at least two sites of a tibialis posterior muscle adjoining said clubfoot-affected foot.

A method of reducing equinus in a relapsed clubfoot-affected foot of a patient, the method comprising;
   injecting a medicament comprising a neuromuscular paralytic agent into at least four sites of a gastrosoleus muscle complex adjoining said clubfoot-affected foot.

A method of reducing adductus in a relapsed clubfoot-affected foot of a patient, the method comprising;
   injecting a medicament comprising a neuromuscular paralytic agent into at least 1 site of an abductor hallucis muscle adjoining said clubfoot-affected foot.

The method of any of the above, wherein said tibialis posterior or said abductor hallucis is first identified by use of a muscle stimulator.

The method of any of the above, wherein said neuromuscular paralytic agent is an acetylcholine antagonist.

The method of any of the above, wherein said acetylcholine antagonist is a botulinum toxin.

The method of any of the above, wherein said botulinum toxin is botulinum toxin type A.

The method of any of the above, wherein said medicament is selected from the group of Botox™ and Myobloc™.

The method of any of the above, wherein said injection is followed by casting of said clubfoot affected foot.

What is claimed is:

1. A method of treating a patient with relapsed clubfoot, the method comprising: injecting an effective amount of a medicament comprising a botulinum toxin into at least two sites of a muscle adjoining said clubfoot-affected foot, said muscle selected from the group consisting of a tibialis posterior, gastrosoleus complex and abductor hallucis; correcting the position of the patient's clubfoot-affected foot after injection of said botulinum toxin and applying a first cast to the clubfoot-affected foot; permitting the patient to fully weight bear on the first cast; removing the first cast; and applying a second cast to the patient's clubfoot-affected foot, wherein the patient has not undergone previous invasive intervention, to thereby obtain correction after relapse and thereby treat the patient.

2. The method of claim 1, wherein the botulinum toxin is selected from the group consisting of botulinum toxin type A, B, C, D, E, F and G.

3. The method of claim 2, wherein the botulinum toxin is botulinum toxin type A or type B.

4. The method of claim 3, wherein the botulinum toxin is botulinum toxin type A.

5. The method of claim 4, further comprising the step of entering a maintenance bracing program.

6. The method of claim 5, wherein a brace of the maintenance bracing program is worn about 12 hours per day.

7. The method of claim 5, wherein a brace of the maintenance bracing program is worn full time.

8. The method of claim 7, wherein a brace of the maintenance bracing program is worn full time for 3 months, followed by nighttime wear.

9. The method of claim 8, wherein nighttime wear is maintained until the brace is outgrown by the patient.

10. The method of claim 3, wherein the patient fully bears weight on the first cast for 2 to 3 weeks.

11. The method of claim 1, further comprising the step of massaging the muscle after the injecting step.

12. A method of treating a patient with relapsed clubfoot, the method comprising: administering a pharmacologically effective amount of a medicament containing a botulinum toxin into at least two sites of a tibialis posterior muscle, wherein the patient's clubfoot-affected foot before administration is in supination and the patient has not undergone previous invasive intervention; performing above-knee manipulation to correct the position of the patient's clubfoot-affected foot; applying a above-knee cast; allowing the patient to fully weight bear on the first above-knee cast ad libidum, performing below knee-manipulation and changing said above-knee cast for a below-knee cast; and entering a maintenance bracing program after removal of the below-knee cast, thereby treating the patient by obtaining correction after relapse.

13. The method of claim 12, wherein the botulinum toxin is selected from the group consisting of botulinum toxin type A, B, C, D, E, F and G.

14. The method of claim 13, wherein the botulinum toxin is botulinum toxin type A or type B.

15. A method of treating a patient with relapsed clubfoot, the method comprising: administering a pharmacologically effective amount of a medicament containing a botulinum toxin into at least four sites of a gastrosoleus complex muscle, wherein the patient's clubfoot-affected foot before administration is in equinus and the patient has not undergone previous invasive intervention; performing manipulation to position the patient's clubfoot-affected foot in a dorsiflexion posture; applying a below-knee cast; allowing the patient to fully weight bear on the below-knee cast ad libidum; removing the below-knee cast and again positioning the clubfoot-affected foot in a dorsiflexion posture and applying a second cast; and entering a maintenance bracing program after removal of the second cast, thereby treating the patient by obtaining correction after relapse.

16. The method of claim 15, wherein the botulinum toxin is botulinum toxin type A.

17. The method of claim 16, wherein administration is performed in a stellate pattern.

18. The method of claim 17, wherein the administration includes administration to a distal soleus muscle.

19. The method of claim 18, further comprising administration of botulinum toxin type A to at least one of a tibialis posterior or abductor hallucis.

20. The method of claim 19, wherein the maintenance bracing program is three months long.

* * * * *

UNITED STATES PATENT AND TRADEMARK OFFICE
CERTIFICATE OF CORRECTION

PATENT NO. : 7,820,183 B2
APPLICATION NO. : 11/504198
DATED : October 26, 2010
INVENTOR(S) : Christine M. Alvarez It is certified that error appears in the above-identified patent and that said Letters Patent is hereby corrected as shown below:

Title Page, item (56), under "Other Publications", delete "Applington" and insert -- Aplington --, therefor.

On the first page, in field (56), under "Other Publications", delete "fouir" and insert -- four --, therefor.

On page 2, under "Other Publications", line 1, delete "roentogenographic" and insert -- roentgenographic --, therefor.

On page 2, in column 1, under "Other Publications", line 11, delete "cloub foot" and insert -- clubfoot --, therefor.

On page 2, in column 2, under "Other Publications", line 8, delete "Orthopetic." and insert -- Orthopedic. --, therefor.

In column 1, line 42, delete "(Applington" and insert -- (Aplington --, therefor.

In column 1, line 48, delete "MOS" and insert -- AAOS --, therefor.

In column 1, line 50, delete "roentogenographic" and insert -- roentgenographic --, therefor.

In column 1, line 51, delete "Sift" and insert -- Siff --, therefor.

In column 3, line 15, delete "eith" and insert -- with --, therefor.

In column 5, line 11, delete "myelomenginocoele, arthrgryposis," and insert -- myelomeningocele, arthrogryposis, --, therefor.

In column 5, line 12, delete "deformitie," and insert -- deformities, --, therefor.
In column 5, line 14, delete "unspecificed" and insert -- unspecified --, therefor.

Signed and Sealed this
Nineteenth Day of April, 2011

David J. Kappos
*Director of the United States Patent and Trademark Office*

CERTIFICATE OF CORRECTION (continued)
U.S. Pat. No. 7,820,183 B2

In column 5, line 56, delete "dorsiflexsion," and insert -- dorsiflexion, --, therefor.

In column 6, line 34, delete "compatable." and insert -- compatible. --, therefor.

In column 6, line 59, delete "trochar" and insert -- trocar --, therefor.

In column 7, line 28, delete "l'Appareil" and insert -- l'Appareil --, therefor.

In column 7, line 41, delete "supiation," and insert -- supination, --, therefor.

In column 10, line 42, delete "anaesthetic" and insert -- anaesthetic. A muscle --, therefor.

In column 10, line 48, delete "libidum." and insert -- libitum. --, therefor.

In column 11, line 2, delete "libidum." and insert -- libitum. --, therefor.

In column 11, line 20, delete "libidum." and insert -- libitum. --, therefor.

In column 13, line 13, delete "abducutor" and insert -- abductor --, therefor.

In column 15, line 20, in claim 12, delete "libidum," and insert -- libitum; --, therefor.

In column 16, line 10, in claim 15, delete "libidum;" and insert -- libitum; --, therefor.